(12) United States Patent
Chow (10) Patent No.: US 11,103,468 B2
(45) Date of Patent: Aug. 31, 2021

(54) MONO- AND DI-AMIDINE ENDO-EXONUCLEASE INHIBITORS AND METHODS FOR INHIBITING ENDO-EXONUCLEASE ACTIVITY

(71) Applicant: MONTDOREX INC., Ville d'Anjou (CA)

(72) Inventor: Terry Chow, Ville d'Anjou (CA)

(*) Notice: Subject to any disclaimer, the term of this patent is extended or adjusted under 35 U.S.C. 154(b) by 0 days.

(21) Appl. No.: 16/759,768

(22) PCT Filed: Nov. 8, 2018

(86) PCT No.: PCT/CA2018/051409
§ 371 (c)(1),
(2) Date: Apr. 28, 2020

(87) PCT Pub. No.: WO2019/095046
PCT Pub. Date: May 23, 2019

(65) Prior Publication Data
US 2020/0375924 A1 Dec. 3, 2020

Related U.S. Application Data

(60) Provisional application No. 62/587,118, filed on Nov. 16, 2017.

(51) Int. Cl.
*A61K 31/55* (2006.01)
*A61P 35/00* (2006.01)
*A61K 31/155* (2006.01)

(52) U.S. Cl.
CPC ............ *A61K 31/155* (2013.01); *A61P 35/00* (2018.01)

(58) Field of Classification Search
CPC .................. A61K 31/55; A61P 35/00
See application file for complete search history.

(56) References Cited

U.S. PATENT DOCUMENTS

| 4,598,077 A | 7/1986 | Fujii et al. |
| 5,324,830 A | 6/1994 | Resnick et al. |

(Continued)

FOREIGN PATENT DOCUMENTS

| CA | 2388674 A1 | 5/2001 |
| CN | 101481332 A | 7/2009 |

(Continued)

OTHER PUBLICATIONS

Ferroni, R., et al—"N1-Substituted benzamidines: synthesis, antiproteinase activity and inhibition of tumor cell growth(')", Farmaco, 1991,46(11), p. 1311-21 (Year: 1991).*

(Continued)

*Primary Examiner* — Craig D Ricci
*Assistant Examiner* — Janet L Coppins
(74) *Attorney, Agent, or Firm* — Anglehart et al.

(57) ABSTRACT

Compounds useful in inhibiting endo-exonuclease activity and treating cancer have the formula (I) wherein R3 is selected from the group consisting of loweralkyl, oxyalkyl, cycloalkyl, aryl, heteroaryl, heterocycloalkyl, aminoalkyl or a halogen; R4 is selected from the group consisting of H, loweralkyl, oxyalkyl, cycloalkyl, aryl, heteroaryl, heterocycloalkyl, aminoalkyl or a halogen; and wherein R5 is a loweralkyl; or formula (II) wherein R1 is selected from the group consisting of loweralkyl, oxyalkyl, cycloalkyl, aryl, heteroaryl, heterocycloalkyl, aminoalkyl or halogen; R2 is selected from the group consisting of H, loweralkyl, oxyalkyl, cycloalkyl, aryl, heteroaryl, heterocycloalkyl, aminoalkyl or halogen; and wherein R5 is a loweralkyl comprising a linear carbon chain of at least two carbons connecting the first "O" to the second "O".

3 Claims, 2 Drawing Sheets

(56) References Cited

U.S. PATENT DOCUMENTS

| | | |
|---|---|---|
| 5,489,524 A | 2/1996 | Resnick et al. |
| 7,115,665 B1 | 10/2006 | Chow et al. |
| 2005/0272779 A1 | 12/2005 | Edwards et al. |

FOREIGN PATENT DOCUMENTS

| | | |
|---|---|---|
| WO | 2005/079780 A1 | 9/2005 |
| WO | 2016/195077 A1 | 12/2016 |

OTHER PUBLICATIONS

Chow et al, Molecular Cancer Therapeutics 2004, vol. 3(8), Aug. 2004, pp. 911-919. (Year: 2004).*

Ferroni et al, Il Pharmaco 1991, vol. 46 (11), pp. 1311-1321. (Year: 1991).*

International application No. PCT/CA2018/051409 international preliminary report on patentability dated Jan. 30, 2020.

International application No. PCT/CA2018/051409 International Search Report dated Feb. 4, 2019.

International application No. PCT/CA2018/051409 Written Opinion of the International Searching Authority dated Feb. 4, 2019.

International application No. PCT/CA2018/051409 Search Strategy dated Feb. 4, 2019.

Maciejewska, D.; et al.—"Pentamidine analogs: syntheses, structures in solid state by 13C CP/MAS NMR spectroscopy, and X-ray crystallography and their preliminary biological screening against human cancer"—Monatshefiefuer Chemie , 2006, 137(9), 1225-1240.

Ferroni, R., et al—"N1 -Substituted benzamidines: synthesis, antiproteinase activity and inhibition oftumor cell growth(*)", Farmaco, 1991, 46(11), p. 1311-21.

Kandpal, M., et al—"Correlation between inhibition of growth and arginine transport of Leishmania donovani promastigotes in vitro by diamidines"—Lzfe Sciences, 1996, 59(7), p. PL75-80.

Croshaw, B. et al—"Experimental tuberculosis and its chemotherapy"—British Journal of Pharmacology and Chemotherapy, 1950, 5, p. 178-187, See compounds of Group A and Group B on page.

Varkevisser, R., et al—"Structure-activity relationships of pentamidine-affected ion channel trafficking and dofetilide mediated rescue"—British Journal of Pharmacology, 2013, 169(6), p. 1322-1334.

Siboni, R. B., et al—"Biological Efficacy and Toxicity of Diamidines in Myotonic Dystrophy Type 1 Models"—J. Med. Chem., 2015, 58, p. 5770-5780.

Chow et al., (1987) Purification and characterization of an endo-exonuclease activity of yeast that requires a functional RAD52 gene. J. Biol. Chem., 262, 17659-17667.

Chow et al., (1988) An endo-exonuclease activity of yeast that requires a functional RAD52 gene. Mol. Gen. Genet. 211, 41-48.

Sadekova et al., (1997) Induction of PBP74/mortalin/Grp75, a member of the hsp70 family, by low doses of ionizing radiation: a possible role in the induced radioresistance. Int. J. Radiat. Biol. 72, 653-660.

Chow et al., (1983) The identification of a deoxyribonuclease controlled by the RAD52 gene of *Saccharomyces cerevisiae*. In Friedberg, E. C. and Bridges, B. A. (eds), Cellular Responses to DNA Damages. Alan R. Liss, New York, pp. 447-455.

Liu et al., (1995) Mammalian endo-exonuclease activity and its level in various radiation sensitive cell fines. Mutagenesis 10, 91-94.

Niks et al., (1990) Towards an optimized MTT assay. J. Immunol. Methods. 130, 149-151.

Hussain et al., (1993) A new approach for measurement of cytotoxicity using colorimetric assay. J. Immunol. Methods. 160, 89-96.

Yapp et al., (1997) Tumour treatment by sustained intratumoural release of cisplatin: effects of drug alone and combined with radiation. Int. J. Rad. Oncol 39, 497-504.

Chow et al., (2004) The DNA double-stranded break repair protein endo-exonuclease as a therapeutic target for cancer, Molecular Cancer Therapeutics, 3, 911-919.

Hilderbrandt et al., (1998) Identification and Characterization of an Endo/exonuclease in Prteumocystis carinii that is Inhibited by Dicationic Diarylfurans with Efficacy Against Pneumocystis Pneumonia, J Euk. Mzcrobrol., 45, 112-121.

Laemmli, U. K., (1970) Cleavage of structural proteins during the assembly of the head of bacteriophage T4, (1970) Nature 227, 680-685.

Alison H. Harrill et al., (2012) "A Mouse Diversity Panel Approach Reveals the Potential for Clinical Kidney Injury Due to DB289 Not Predicated by Classical Rodent Models", Toxicological Sciences 130(2), 416-426.

Bielawski et al., (2000) Inhibitory effects of pentamidine analogues on protein biosynthesis in vitro. Acta Biochimica Polonica 47:113-120.

* cited by examiner

MONO- AND DI-AMIDINE ENDO-EXONUCLEASE INHIBITORS AND METHODS FOR INHIBITING ENDO-EXONUCLEASE ACTIVITY

The present patent application claims priority from U.S. provisional patent application No. 62/587,118 filed on Nov. 16, 2017.

TECHNICAL FIELD

The present application relates to chemotherapeutic agents for treating cancer and compounds for inhibiting endo-exonuclease activity.

BACKGROUND

Cancer cells proliferate more rapidly than normal cells. The rate of mitosis and DNA replication is therefore significantly greater in cancer cells. Agents that inhibit DNA replication and recombination affect cancer cells more than normal cells.

Many chemotherapeutic agents for treating cancer inhibit DNA replication by inducing DNA breaks. Some drugs, such as mitomycin C, induce DNA breaks in part by its binding to the DNA itself. Other anticancer agents interfere with poly ADP ribose polymerase (PARP) enzymes, which is important for repairing DNA single-stranded breaks. In doing so, they induce strand breaks. Normally the breaks are transient but in the presence of a PARP enzyme inhibitor, such as Olaparib, the breaks become longer lived and expose the DNA to permanent damage.

Living organisms repair DNA by a variety of mechanisms including an excision-repair system. Enzymes that mediate excision-repair cut out the damaged DNA. They then replace the damaged DNA sequences with the correct sequences. Such repair systems lessen the efficiency of cancer therapies that are dependent on chemotherapeutics for inducing DNA breaks. The loss in efficiency necessitates the use of high concentrations of DNA-breaking chemotherapeutics in order to obtain a satisfactory inhibition of cancer proliferation. These chemotherapeutics are very toxic and have damaging side effects. The need to use high concentrations is a significant drawback.

It has been suggested that endo-exonucleases may function in DNA repair and recombination. U.S. Pat. No. 5,324,830 to Resnick et. al. describes the isolation of a DNA segment that codes for an endo-exonuclease, RhoNuc from S. cerevisiae. U.S. Pat. No. 5,489,524 describes the characterization of a gene for mammalian endo-exonuclease and the isolation of primate endo-exonuclease. The endo-exonuclease interacts with various proteins in DNA repair and recombination processes as demonstrated by the "STRING" interaction network. Inhibiting endo-exonuclease activity may be effective for inhibiting the DNA repair process or the proliferation of cancer cells.

U.S. Pat. No. 7,115,665 to Chow et. al. describes interactions between pentamidine and the endo-exonuclease. Moreover, it is further described in Chow et al., "The DNA double-stranded break repair protein endo-exonuclease as a therapeutic target for cancer", in *Molecular Cancer Therapeutics*, 2004, 3(8) p. 911 and following, that increased endo-exonuclease activity is found in a wide variety of different cancer cell lines. This is further illustrated in FIG. 1 of Canadian patent 2,388,674, where the level of endo-exonuclease activity in various cancerous cell lines, compared to a non-cancerous cell line, is shown.

However, there is a need for compounds that inhibit the proliferation of cancer cells that are less toxic than conventional chemotherapeutics. There is a further need for compounds that inhibit DNA recombination repair in order to inhibit the proliferation of cancer cells. There is a further need for compounds that can be used in combination with conventional chemotherapeutics to improve the efficiency of cancer treatment. There is a further need for such compounds to be used in combination with conventional chemotherapeutics so that the combination permits the use of lower dosages of chemotherapeutics to cancer patients without loss of therapeutic efficiency.

SUMMARY

The present application relates to inhibitors of endo-exonuclease. In particular, compounds of diamidine and mono-amidine have been found to exhibit increased endo-exonuclease inhibitory activity when compared to, for example, pentamidine, and can therefore act as anti-cancer agents, e.g., in cases where the cancer cells show an increased endo-exonuclease activity when compared to normal cells.

In a first aspect of the present disclosure, mono-amidine compounds, which may be used, e.g., to inhibit endo-exonuclease activity and/or to treat cancer, such as (without limitation) cancers having an increased endo-exonuclease activity, have the following formula (formula I):

wherein:

$R_3$ is selected from the group consisting of loweralkyl, oxyalkyl, cycloalkyl, aryl, heteroaryl, heterocycloalkyl, aminoalkyl or a halogen;

$R_4$ is selected from the group consisting of H, loweralkyl, oxyalkyl, cycloalkyl, aryl, heteroaryl, heterocycloalkyl, aminoalkyl or a halogen; and $R_5$ is a loweralkyl.

"O" is oxygen.

In some embodiments, $R_5$ may be $(CH_2)_n$, where "n" may be equal to 1, 2, 3, 4, 5, 6, or 7.

In some embodiments, "n" may equal 1 and $R_4$ may be "H".

In some embodiments, "n" may equal 5 and $R_4$ may be "H".

It will be understood that, in some embodiments, the phenyl group of the compound of formula I may have one or more additional substituents.

In some embodiments, $R_3$ may be methyl.

In some embodiments, $R_3$ may be methyl, isopropyl or isobutyl.

In some embodiments, $R_3$ may be isopropyl or isobutyl.

In some embodiments, $R_3$ may be methyl or isobutyl.

In some embodiments, $R_3$ may be methyl or isopropyl.

In some embodiments, $R_3$ may be selected from the group consisting of methyl, propyl or butyl, wherein propyl may be isopropyl or n-propyl, and butyl may be n-butyl, sec-butyl, isobutyl, tert-butyl.

In some embodiments, $R_3$ may be selected from the group consisting of methyl, propyl or butyl, wherein propyl may be cyclopropyl, isopropyl or n-propyl, and butyl may be n-butyl, sec-butyl, isobutyl, tert-butyl.

In some embodiments, R3 may be selected from the group consisting of loweralkyl or aryl.

In some embodiments, R3 may be selected from the group consisting of loweralkyl, oxyalkyl, cycloalkyl, aryl, heteroaryl, heterocycloalkyl or aminoalkyl.

In some embodiments, R3 may be selected from the group consisting of loweralkyl, oxyalkyl, cycloalkyl, aryl, or a halogen.

In some embodiments, R3 may be selected from the group consisting of loweralkyl, oxyalkyl, cycloalkyl or aryl.

In some embodiments, R3 may be selected from the group consisting of loweralkyl, cycloalkyl, aryl, or a halogen.

In some embodiments, R3 may be selected from the group consisting of loweralkyl, cycloalkyl or aryl.

In some embodiments, R3 may be selected from the group consisting of methyl, isopropyl or phenyl.

In some embodiments, R3 may be selected from the group consisting of loweralkyl or phenyl.

In some embodiments, R3 may be selected from the group consisting of methyl, ethyl, propyl, butyl, isobutyl, isopropyl, sec-butyl, tert-butyl, pentyl, isopentyl, and hexyl.

In some embodiments, R3 may be selected from the group consisting of methyl, ethyl, propyl, butyl, isobutyl, isopropyl, sec-butyl, tert-butyl, pentyl, isopentyl, hexyl, and phenyl.

In some embodiments, R3 may be selected from the group consisting of ethyl, propyl, butyl, isobutyl, isopropyl, sec-butyl, tert-butyl, pentyl, isopentyl, hexyl, and phenyl.

In some embodiments, R3 may be selected from the group consisting of propyl, butyl, isobutyl, isopropyl, sec-butyl, tert-butyl, pentyl, isopentyl, hexyl, and phenyl.

In some embodiments, R3 may be selected from the group consisting of butyl, isobutyl, isopropyl, sec-butyl, tert-butyl, pentyl, isopentyl, hexyl, and phenyl.

In some embodiments, R3 may be selected from the group consisting of isobutyl, isopropyl, sec-butyl, tert-butyl, pentyl, isopentyl, hexyl, and phenyl.

In some embodiments, R3 may be isopropyl.

In some embodiments, R4 may be H and n may equal 1.

In some embodiments, R4 may be a loweralkyl.

In some embodiments, R4 may be selected from the group consisting of loweralkyl, oxyalkyl, cycloalkyl, aryl, heteroaryl, heterocycloalkyl, aminoalkyl or a halogen.

In some embodiments, R4 may be selected from the group consisting of H or loweralkyl.

In some embodiments, R4 may be selected from the group consisting of H, loweralkyl or a halogen.

In some embodiments, R4 may be selected from the group consisting of H, loweralkyl, cycloalkyl, aryl, or a halogen.

In some embodiments, R4 may be selected from the group consisting of H, loweralkyl, cycloalkyl or aryl.

In some embodiments, R4 may be selected from the group consisting of H, loweralkyl, oxyalkyl, cycloalkyl, aryl or a halogen.

In some embodiments, R4 may be selected from the group consisting of H, loweralkyl, oxyalkyl, cycloalkyl or aryl.

In some embodiments, R3 may be a loweralkyl.

In some embodiments, R3 may be selected from the group consisting of cyclopropylmethyl, cyclobutyl, 3,4,5,6-tetrahydropyrimidyl, cyclopropyl, cyclopentyl or isobutyl.

In some embodiments, R3 may be selected from the group consisting of cyclopropylmethyl, cyclobutyl, 3,4,5,6-tetrahydropyrimidyl, cyclopropyl, cyclopentyl, isobutyl or isopropyl.

In some embodiments, R3 may be selected from the group consisting of cyclopropylmethyl, cyclobutyl, 3,4,5,6-tetrahydropyrimidyl, cyclopropyl, cyclopentyl, isobutyl, isopropyl, methyl or phenyl.

In some embodiments, R3 may be selected from the group consisting of cyclopropylmethyl, cyclobutyl, 3,4,5,6-tetrahydropyrimidyl, cyclopropyl, cyclopentyl, isobutyl, isopropyl or phenyl.

In some embodiments, R3 may be selected from the group consisting of cyclopropylmethyl, cyclobutyl, cyclopropyl, cyclopentyl, isobutyl, isopropyl or phenyl.

In some embodiments, R3 may be selected from the group consisting of cyclobutyl, 3,4,5,6-tetrahydropyrimidyl, cyclopropyl, cyclopentyl, isobutyl, isopropyl or phenyl.

In some embodiments, R3 may be selected from the group consisting of cyclopropylmethyl, 3,4,5,6-tetrahydropyrimidyl, cyclopropyl, cyclopentyl, isobutyl, isopropyl or phenyl.

In some embodiments, R3 may be selected from the group consisting of cyclopropylmethyl, cyclobutyl, 3,4,5,6-tetrahydropyrimidyl, cyclopentyl, isobutyl, isopropyl or phenyl.

In some embodiments, R3 may be selected from the group consisting of cyclopropylmethyl, cyclobutyl, 3,4,5,6-tetrahydropyrimidyl, cyclopropyl, isobutyl, isopropyl or phenyl.

In some embodiments, R3 may be selected from the group consisting of cyclopropylmethyl, cyclobutyl, 3,4,5,6-tetrahydropyrimidyl, cyclopropyl, cyclopentyl, isopropyl or phenyl.

In some embodiments, R3 may be selected from the group consisting of cyclobutyl, 3,4,5,6-tetrahydropyrimidyl, cyclopropyl, cyclopentyl, isobutyl or isopropyl.

In some embodiments, R3 may be selected from the group consisting of cyclopropylmethyl, 3,4,5,6-tetrahydropyrimidyl, cyclopropyl, cyclopentyl, isobutyl or isopropyl.

In some embodiments, R3 may be selected from the group consisting of cyclopropylmethyl, cyclobutyl, cyclopropyl, cyclopentyl, isobutyl or isopropyl.

In some embodiments, R3 may be selected from the group consisting of cyclopropylmethyl, cyclobutyl, 3,4,5,6-tetrahydropyrimidyl, cyclopentyl, isobutyl or isopropyl.

In some embodiments, R3 may be selected from the group consisting of cyclopropylmethyl, cyclobutyl, 3,4,5,6-tetrahydropyrimidyl, cyclopropyl, isobutyl or isopropyl.

In some embodiments, R3 may be selected from the group consisting of cyclopropylmethyl, cyclobutyl, 3,4,5,6-tetrahydropyrimidyl, cyclopropyl, cyclopentyl or isopropyl.

In another aspect of the present disclosure, diamidine compounds, which may be used, e.g., to inhibit endo-exonuclease activity and/or to treat cancer, such as (without limitation) cancers having an increased endo-exonuclease activity, have the following formula (formula II):

wherein:
R1 and is selected from the group consisting of loweralkyl, oxyalkyl, cycloalkyl, aryl, heteroaryl, heterocycloalkyl, aminoalkyl or a halogen;
R2 is selected from the group consisting of: H, loweralkyl, oxyalkyl, cycloalkyl, aryl, heteroaryl, heterocycloalkyl, aminoalkyl or a halogen; and R5 is a loweralkyl comprising a linear carbon chain of at least two carbons connecting the first "O" to the second "O". "O" is oxygen.

In some embodiments, R5 may be $(CH_2)_n$, and "n" of "$(CH_2)_n$," may be equal to 2, 3, 4, 5, 6, or 7.

In some embodiments, "n" may equal 5.

In some embodiments, R2 may be selected from the group consisting of:

loweralkyl, oxyalkyl, cycloalkyl, aryl, heteroaryl, heterocycloalkyl, aminoalkyl or a halogen.

In some embodiments, the phenyl groups may have one or more additional substituents.

In some embodiments, R1 may be isopropyl.

In some embodiments, R1 may be phenyl.

In some embodiments, R1 may be H.

In some embodiments, R2 may be isopropyl.

In some embodiments, R2 may be phenyl.

In some embodiments, R1 may be methyl.

In some embodiments, R1 may be selected from the group consisting of loweralkyl or aryl.

In some embodiments, R1 may be selected from the group consisting of loweralkyl, oxyalkyl, cycloalkyl, aryl, heteroaryl, heterocycloalkyl or aminoalkyl.

In some embodiments, R1 may be selected from the group consisting of loweralkyl, oxyalkyl, cycloalkyl, aryl, or a halogen.

In some embodiments, R1 may be selected from the group consisting of loweralkyl, oxyalkyl, cycloalkyl or aryl.

In some embodiments, R1 may be selected from the group consisting of loweralkyl, cycloalkyl, aryl, or a halogen.

In some embodiments, R1 may be selected from the group consisting of loweralkyl, cycloalkyl or aryl.

In some embodiments, R1 may be selected from the group consisting of methyl, isopropyl, isobutyl or phenyl.

In some embodiments, R1 may be selected from the group consisting of propyl, butyl or phenyl, wherein propyl may be isopropyl or n-propyl, and butyl may be n-butyl, sec-butyl, isobutyl or tert-butyl.

In some embodiments, R1 may be selected from the group consisting of propyl, butyl or phenyl, wherein propyl may be cyclopropyl, isopropyl or n-propyl, and butyl may be n-butyl, sec-butyl, isobutyl or tert-butyl.

In some embodiments, R1 may be selected from the group consisting of isopropyl, isobutyl or phenyl.

In some embodiments, R1 may be selected from the group consisting of methyl, isobutyl or phenyl.

In some embodiments, R1 may be selected from the group consisting of methyl, isopropyl or phenyl.

In some embodiments, R1 may be selected from the group consisting of methyl, isopropyl or isobutyl.

In some embodiments, R1 may be selected from the group consisting of isopropyl or phenyl.

In some embodiments, R1 may be selected from the group consisting of loweralkyl or phenyl.

In some embodiments, R1 may be selected from the group consisting of methyl, ethyl, propyl, butyl, isobutyl, isopropyl, sec-butyl, tert-butyl, pentyl, isopentyl, and hexyl.

In some embodiments, R1 may be selected from the group consisting of methyl, ethyl, propyl, butyl, isobutyl, isopropyl, sec-butyl, tert-butyl, pentyl, isopentyl, hexyl, and phenyl.

In some embodiments, R1 may be selected from the group consisting of ethyl, propyl, butyl, isobutyl, isopropyl, sec-butyl, tert-butyl, pentyl, isopentyl, hexyl, and phenyl.

In some embodiments, R1 may be selected from the group consisting of propyl, butyl, isobutyl, isopropyl, sec-butyl, tert-butyl, pentyl, isopentyl, hexyl, and phenyl.

In some embodiments, R1 may be selected from the group consisting of butyl, isobutyl, isopropyl, sec-butyl, tert-butyl, pentyl, isopentyl, hexyl, and phenyl.

In some embodiments, R1 may be selected from the group consisting of isobutyl, isopropyl, sec-butyl, tert-butyl, pentyl, isopentyl, hexyl, and phenyl.

In some embodiments, R1 may be isopropyl.

In some embodiments, R1 may be a loweralkyl.

In some embodiments, R1 may be selected from the group consisting of cyclopropylmethyl, cyclobutyl, 3,4,5,6-tetrahydropyrimidyl, cyclopropyl, cyclopentyl or isobutyl.

In some embodiments, R1 may be selected from the group consisting of cyclopropylmethyl, cyclobutyl, 3,4,5,6-tetrahydropyrimidyl, cyclopropyl, cyclopentyl, isobutyl or isopropyl.

In some embodiments, R1 may be selected from the group consisting of cyclopropylmethyl, cyclobutyl, 3,4,5,6-tetrahydropyrimidyl, cyclopropyl, cyclopentyl, isobutyl, isopropyl, methyl or phenyl.

In some embodiments, R1 may be selected from the group consisting of cyclopropylmethyl, cyclobutyl, 3,4,5,6-tetrahydropyrimidyl, cyclopropyl, cyclopentyl, isobutyl, isopropyl or phenyl.

In some embodiments, R1 may be selected from the group consisting of cyclopropylmethyl, cyclobutyl, cyclopropyl, cyclopentyl, isobutyl, isopropyl or phenyl.

In some embodiments, R1 may be selected from the group consisting of cyclobutyl, 3,4,5,6-tetrahydropyrimidyl, cyclopropyl, cyclopentyl, isobutyl, isopropyl or phenyl.

In some embodiments, R1 may be selected from the group consisting of cyclopropylmethyl, 3,4,5,6-tetrahydropyrimidyl, cyclopropyl, cyclopentyl, isobutyl, isopropyl or phenyl.

In some embodiments, R1 may be selected from the group consisting of cyclopropylmethyl, cyclobutyl, 3,4,5,6-tetrahydropyrimidyl, cyclopentyl, isobutyl, isopropyl or phenyl.

In some embodiments, R1 may be selected from the group consisting of cyclopropylmethyl, cyclobutyl, 3,4,5,6-tetrahydropyrimidyl, cyclopropyl, isobutyl, isopropyl or phenyl.

In some embodiments, R1 may be selected from the group consisting of cyclopropylmethyl, cyclobutyl, 3,4,5,6-tetrahydropyrimidyl, cyclopropyl, cyclopentyl, isopropyl or phenyl.

In some embodiments, R1 may be selected from the group consisting of cyclobutyl, 3,4,5,6-tetrahydropyrimidyl, cyclopropyl, cyclopentyl, isobutyl or isopropyl.

In some embodiments, R1 may be selected from the group consisting of cyclopropylmethyl, 3,4,5,6-tetrahydropyrimidyl, cyclopropyl, cyclopentyl, isobutyl or isopropyl.

In some embodiments, R1 may be selected from the group consisting of cyclopropylmethyl, cyclobutyl, cyclopropyl, cyclopentyl, isobutyl or isopropyl.

In some embodiments, R1 may be selected from the group consisting of cyclopropylmethyl, cyclobutyl, 3,4,5,6-tetrahydropyrimidyl, cyclopentyl, isobutyl or isopropyl.

In some embodiments, R1 may be selected from the group consisting of cyclopropylmethyl, cyclobutyl, 3,4,5,6-tetrahydropyrimidyl, cyclopropyl, isobutyl or isopropyl.

In some embodiments, R1 may be selected from the group consisting of cyclopropylmethyl, cyclobutyl, 3,4,5,6-tetrahydropyrimidyl, cyclopropyl, cyclopentyl or isopropyl.

In some embodiments, R2 may be methyl.

In some embodiments, R2 may be selected from the group consisting of loweralkyl or aryl.

In some embodiments, R2 may be selected from the group consisting of loweralkyl, oxyalkyl, cycloalkyl, aryl, heteroaryl, heterocycloalkyl or aminoalkyl.

In some embodiments, R2 may be selected from the group consisting of loweralkyl, oxyalkyl, cycloalkyl, aryl, or a halogen.

In some embodiments, R2 may be selected from the group consisting of loweralkyl, oxyalkyl, cycloalkyl or aryl.

In some embodiments, R2 may be selected from the group consisting of loweralkyl, cycloalkyl, aryl, or a halogen.

In some embodiments, R2 may be selected from the group consisting of loweralkyl, cycloalkyl or aryl.

In some embodiments, R2 may be selected from the group consisting of methyl, isopropyl, isobutyl or phenyl.

In some embodiments, R2 may be selected from the group consisting of propyl, butyl or phenyl, wherein propyl may be isopropyl or n-propyl, and butyl may be n-butyl, sec-butyl, isobutyl or tert-butyl.

In some embodiments, R2 may be selected from the group consisting of propyl, butyl or phenyl, wherein propyl may be cyclopropyl, isopropyl or n-propyl, and butyl may be n-butyl, sec-butyl, isobutyl or tert-butyl.

In some embodiments, R2 may be selected from the group consisting of isopropyl, isobutyl or phenyl.

In some embodiments, R2 may be selected from the group consisting of methyl, isobutyl or phenyl.

In some embodiments, R2 may be selected from the group consisting of methyl, isopropyl or phenyl.

In some embodiments, R2 may be selected from the group consisting of methyl, isopropyl or isobutyl.

In some embodiments, R2 may be selected from the group consisting of isopropyl or phenyl.

In some embodiments, R2 may be selected from the group consisting of loweralkyl or phenyl.

In some embodiments, R2 may be selected from the group consisting of methyl, ethyl, propyl, butyl, isobutyl, isopropyl, sec-butyl, tert-butyl, pentyl, isopentyl, and hexyl.

In some embodiments, R2 may be selected from the group consisting of methyl, ethyl, propyl, butyl, isobutyl, isopropyl, sec-butyl, tert-butyl, pentyl, isopentyl, hexyl, and phenyl.

In some embodiments, R2 may be selected from the group consisting of ethyl, propyl, butyl, isobutyl, isopropyl, sec-butyl, tert-butyl, pentyl, isopentyl, hexyl, and phenyl.

In some embodiments, R2 may be selected from the group consisting of propyl, butyl, isobutyl, isopropyl, sec-butyl, tert-butyl, pentyl, isopentyl, hexyl, and phenyl.

In some embodiments, R2 may be selected from the group consisting of butyl, isobutyl, isopropyl, sec-butyl, tert-butyl, pentyl, isopentyl, hexyl, and phenyl.

In some embodiments, R2 may be selected from the group consisting of isobutyl, isopropyl, sec-butyl, tert-butyl, pentyl, isopentyl, hexyl, and phenyl.

In some embodiments, R2 may be isopropyl.

In some embodiments, R2 may be a loweralkyl.

In some embodiments, R2 may be selected from the group consisting of cyclopropylmethyl, cyclobutyl, 3,4,5,6-tetrahydropyrimidyl, cyclopropyl, cyclopentyl or isobutyl.

In some embodiments, R2 may be selected from the group consisting of cyclopropylmethyl, cyclobutyl, 3,4,5,6-tetrahydropyrimidyl, cyclopropyl, cyclopentyl, isobutyl or isopropyl.

In some embodiments, R2 may be selected from the group consisting of cyclopropylmethyl, cyclobutyl, 3,4,5,6-tetrahydropyrimidyl, cyclopropyl, cyclopentyl, isobutyl, isopropyl, methyl or phenyl.

In some embodiments, R2 may be selected from the group consisting of cyclopropylmethyl, cyclobutyl, 3,4,5,6-tetrahydropyrimidyl, cyclopropyl, cyclopentyl, isobutyl, isopropyl or phenyl.

In some embodiments, R2 may be selected from the group consisting of cyclopropylmethyl, cyclobutyl, cyclopropyl, cyclopentyl, isobutyl, isopropyl or phenyl.

In some embodiments, R2 may be selected from the group consisting of cyclobutyl, 3,4,5,6-tetrahydropyrimidyl, cyclopropyl, cyclopentyl, isobutyl, isopropyl or phenyl.

In some embodiments, R2 may be selected from the group consisting of cyclopropylmethyl, 3,4,5,6-tetrahydropyrimidyl, cyclopropyl, cyclopentyl, isobutyl, isopropyl or phenyl.

In some embodiments, R2 may be selected from the group consisting of cyclopropylmethyl, cyclobutyl, 3,4,5,6-tetrahydropyrimidyl, cyclopentyl, isobutyl, isopropyl or phenyl.

In some embodiments, R2 may be selected from the group consisting of cyclopropylmethyl, cyclobutyl, 3,4,5,6-tetrahydropyrimidyl, cyclopropyl, isobutyl, isopropyl or phenyl.

In some embodiments, R2 may be selected from the group consisting of cyclopropylmethyl, cyclobutyl, 3,4,5,6-tetrahydropyrimidyl, cyclopropyl, cyclopentyl, isopropyl or phenyl.

In some embodiments, R2 may be selected from the group consisting of cyclobutyl, 3,4,5,6-tetrahydropyrimidyl, cyclopropyl, cyclopentyl, isobutyl or isopropyl.

In some embodiments, R2 may be selected from the group consisting of cyclopropylmethyl, 3,4,5,6-tetrahydropyrimidyl, cyclopropyl, cyclopentyl, isobutyl or isopropyl.

In some embodiments, R2 may be selected from the group consisting of cyclopropylmethyl, cyclobutyl, cyclopropyl, cyclopentyl, isobutyl or isopropyl.

In some embodiments, R2 may be selected from the group consisting of cyclopropylmethyl, cyclobutyl, 3,4,5,6-tetrahydropyrimidyl, cyclopentyl, isobutyl or isopropyl.

In some embodiments, R2 may be selected from the group consisting of cyclopropylmethyl, cyclobutyl, 3,4,5,6-tetrahydropyrimidyl, cyclopropyl, isobutyl or isopropyl.

In some embodiments, R2 may be selected from the group consisting of cyclopropylmethyl, cyclobutyl, 3,4,5,6-tetrahydropyrimidyl, cyclopropyl, cyclopentyl or isopropyl.

All of the above-described sub-groups of R3, R4 and n may be combined in any manner and all such combinations are deemed to be disclosed herein for the purpose of original written disclosure, as well as for the purpose of restricting the claimed subject matter.

In addition to the compounds according to formula (I) and formula (II) described above, as well as any further compounds disclosed below, also disclosed herein are pharmaceutically acceptable salts thereof, pharmaceutical compositions containing the same, and the use of any of the above-described compounds and/or pharmaceutically acceptable salts thereof for the preparation of a medicament for the treatment of cancer, such as (without limitation) cancers having an increased endo-exonuclease activity.

According to another aspect of the present teachings, any of the compounds according to formula (I) and formula (II) described above, as well as any further compounds disclosed below, may be provided in combination with one or more known chemotherapeutic drugs that cause breaks in DNA, to provide medicaments that inhibit the proliferation of cancer cells and tumour growth. Furthermore, methods of inhibiting the proliferation of cancer cells and tumour growth are also disclosed herein, and may preferably comprise: administering to a patient in need thereof a therapeutically-effective amount of any compound disclosed herein that inhibits the activity of endo-exonuclease in combination with a therapeutically-effective amount of one or more known chemotherapeutic drugs that cause breaks in DNA. Therefore, compounds of the present disclosure that, e.g., inhibit the activity of endo-exonuclease, may be administered in combination with agents that cause breaks in DNA to inhibit the proliferation of cancer cells and tumour growth. Such combinations of compounds may be provided in a pharmaceutically acceptable carrier to provide pharmaceutical compositions according to the present disclosure.

In another aspect of the present disclosure, methods of treating a patient having cancerous cells are disclosed. Such methods preferably include administering, to the patient, a therapeutically effective amount of a compound having the formula (formula I):

wherein R3, R4 and R5 may be selected according to any of the groups or sub-groups of R3, R4 and R5 disclosed above or below, e.g., in an amount effective to inhibit the proliferation of the cancer cells or to inhibit tumour growth composed of the cancer cells in the patient. In some embodiments, a compound of the present disclosure may be administered to a patent having cancerous cells that exhibit elevated endo-exonuclease activity in comparison to average endo-exonuclease activity of normal cells.

In some embodiments, the method may include also administering (e.g., co-administering) a therapeutically effective amount of a chemotherapeutic agent that induces breaks in DNA (e.g., a nuclease), representative non-limiting examples of which will be enumerated below.

In some embodiments, the chemotherapeutic agent that is administered may induce double-stranded breaks in DNA.

In some embodiments, the chemotherapeutic agent that is administered may be selected from at least one of cisplatin, mitomycin C, melphalan, Adriamycin, taxol, 5-fluoro-uracil, carmustine, and bleomycin.

In some embodiments, the method may further include administering ionizing radiation.

In another aspect of the present disclosure, methods of treating a patient having cancerous cells may include administering to the patient a compound having the formula (formula II):

wherein R1, R2 and R5 may be selected according to any of the groups or sub-groups of R1, R2 and R5 disclosed above or below, e.g., in an amount effective to inhibit the proliferation of the cancer cells or to inhibit tumour growth composed of the cancer cells in the patient.

In some embodiments, any of such compounds of the present disclosure also may be administered to a patient having cancerous cells that exhibit elevated endo-exonuclease activity in comparison to average endo-exonuclease activity of normal cells.

In some embodiments, such a method may include administering (e.g., co-administering) a therapeutically effective amount of a chemotherapeutic agent that induces breaks in DNA (e.g., a nuclease), representative non-limiting examples of which will be enumerated below.

In some embodiments, the chemotherapeutic agent that is administered may induce double-stranded breaks in DNA.

In some embodiments, the chemotherapeutic agent that is administered may be selected from at least one of cisplatin, mitomycin C, melphalan, Adriamycin, taxol, 5-fluoro-uracil, carmustine, and bleomycin.

In some embodiments, the method may include administering ionizing radiation.

In another aspect of the present disclosure, pharmaceutical compositions, e.g., for treating cancer, e.g., cancers in which the cancer cells exhibit increased endo-exonuclease activity in comparison to endo-exonuclease activity of normal cells, are also disclosed. Such pharmaceutical compositions preferably include any of the mono-amidine or di-amidine compounds disclosed above or below.

In some embodiments, the pharmaceutical composition is effective for treating cancer having increased endo-exonuclease activity in comparison to endo-exonuclease activity of normal cells.

In some embodiments, the pharmaceutical composition may further include a chemotherapeutic agent that induces breaks in DNA.

In some embodiments, the chemotherapeutic agent may induce double-stranded breaks in DNA.

In some embodiments, the chemotherapeutic agent may be selected from at least one of cisplatin, mitomycin C, melphalan, Adriamycin, taxol, 5-fluoro-uracil, carmustine, and bleomycin.

In some embodiments, the pharmaceutical composition may be provided in a pharmaceutically acceptable carrier.

In some embodiments, the pharmaceutical composition may include an agent that sensitizes the cancer cells to the agent that induces DNA breaks and/or to the compound that inhibits endo-exonuclease activity.

In some embodiments, the composition may include an agent that sensitizes the cancer cells to the agent that induces DNA breaks and/or to the compound that inhibits endo-exonuclease activity.

In some embodiments, the compound of formula I, a pharmaceutically effective salt thereof, the compound of formula II and/or a pharmaceutically effective salt thereof, may be used to inhibit endo-exonuclease activity. In some embodiments, the endo-exonuclease may be a human endo-exonuclease activity.

The present disclosure also pertains to use of the compound of formula I, a pharmaceutically effective salt thereof, the compound of formula II and/or a pharmaceutically effective salt thereof, to inhibit endo-exonuclease activity. In some embodiments, the endo-exonuclease activity may be human endo-exonuclease activity.

BRIEF DESCRIPTION OF THE DRAWING

The invention will be better understood by way of the following detailed description of representative, non-limiting embodiments of the invention with reference to the appended drawing, in which.

DETAILED DESCRIPTION

DEFINITIONS

The term "aminoalkyl" as used herein refers to a C1-C7, saturated or unsaturated, linear or branched alkyl joined to an amino group ($NH_2$). Examples of aminoalkyl include, but are not limited to, $—CH_2NH_2$, $—CH_2CH_2NH_2$, etc. An aminoalkyl may be optionally substituted with one or more (e.g. one to five) substituents independently selected from, for instance, the group consisting of hydroxy, thiol, cyano, nitro, loweralkyl, sulfonyl, halogen or amino.

The term "aryl" as used herein refers to a six to ten membered monocyclic or polycyclic aromatic ring where all of the ring atoms are carbon atoms. Examples of aryls include but are not limited to phenyl and biphenyl. An aryl may be optionally substituted with one to five substituents independently selected from, for instance, the group consisting of hydroxy, thiol, cyano, nitro, loweralkyl, sulfonyl, halogen or amino.

The term "cycloalkyl" as used herein, refers to a three to ten membered monocyclic or polycyclic ring, saturated or partially unsaturated, where all of the ring atoms are carbon. Examples of cycloalkyl include, but are not limited to, cyclopropyl, cyclobutyl, cyclopentyl, cyclopentenyl, cyclohexyl, cyclohexenyl, etc. A cycloalkyl may be optionally substituted by one to five substituents independently selected from, for instance, the group consisting of hydroxy, thiol, cyano, nitro, loweralkyl, sulfonyl, halogen or amino.

The term "heteroaryl" as used herein refers to a five to ten membered monocyclic or polycyclic aromatic ring having atoms selected from N, O, S and C. Examples of heteroaryl include, but are not limited to, furanyl, thienyl, imidazolyl, pyrazolyl, pyrrolyl, pyrrolinyl, thiazolyl, etc. An heteroaryl may be optionally substituted with one to five substituents independently selected from, for instance, the group consisting of hydroxy, thiol, cyano, nitro, loweralkyl, sulfonyl, halogen or amino.

The term "heterocycloalkyl" as used herein refers to a four to ten membered monocyclic or polycyclic ring, saturated or partially unsaturated, where the ring atoms are selected from N, O, S and C. Examples of heterocycloalkyl include, but are not limited to, azetidinyl, tetrahydrofuran, dihydrofuran, dioxane, morpholine, etc. A heterocycloalkyl may be optionally substituted by one to five substituents independently selected from, for instance, the group consisting of hydroxy, thiol, cyano, nitro, loweralkyl, sulfonyl, halogen or amino.

The term "loweralkoxy" or "oxyalkyl" as used herein, refers to C1-C7, saturated or unsaturated, linear or branched alkoxy, such as methoxy, ethoxy, propyloxy, butyloxy, isopropyloxy, and t-butyloxy. A loweralkoxy or oxyalkyl may be optionally substituted with one or more (e.g. one to five) substituents independently selected from, for instance, the group consisting of hydroxy, thiol, cyano, nitro, loweralkyl, sulfonyl, halogen or amino.

The term "loweralkyl," as used herein, refers to C1-C7, saturated or unsaturated (e.g. one or more double or triple bonds), linear or branched alkyl, such as methyl, ethyl, propyl, butyl, isobutyl, isopropyl, sec-butyl, tert-butyl, pentyl, isopentyl, and hexyl. A loweralkyl may be optionally substituted with one or more (e.g. one to five) substituents independently selected from, for instance, the group consisting of hydroxy, thiol, cyano, nitro, loweralkyl, sulfonyl, halogen or amino.

INTRODUCTION

It was previously known that some amidines have anti-fungal and anti-microbial activity. In the article "Identification and Characterization of an Endo/exonuclease in *Pneumocystis carinii* that is Inhibited by Dicatonic Diary Ifurans with Efficacy Against *Pneumocystis* Pneumonia" by Ellen Hildebrandt et al., 1998, *J. Euk. Microbial,* 45(1), 1998 pp. 112-121, it was shown that a diarylfuran, 2,5-bis[4-(N-isopropylguanyl)phenyl]furan, inhibits endo-exonuclease activity present in certain bacteria, such as *Pneumocystis carinii*. Similarly, it was also shown that 2,5-bis[4-[(N-cyclopropylmethylguanyl)phenyl]furan, 2,5-bis[(4-N-cyclobutylgunayl)phenyl]furan, 2,5-bis-p[3,4,5,6-tetrahydropyrimidyl)phenyl]furan, 2,5-bis [4-N-(cyclopropylguanyl)phenyl] furan, 2,5-bis[(4-N-cyclopentylguanyl)phenyl] furan, 2,5-bis[4-guanylphenyl]furan and 2,5-bis[4-N-isobutylguanyl)phenyl]furan showed nuclease inhibition activity in *P. Carinii*, an infectious bacterial strain.

Moreover, it had been observed that pentamidine has demonstrated inhibitory activity of the human endo-exonuclease and can therefore be used as an anti-cancer agent in humans where the cancerous cells show an increase endo-exonuclease activity.

Applicant has studied and observed that mono-amidine and di-amidine compounds, where the hydrogen(s) of the sp3 nitrogen of the amidine group is/are replaced with a substitute group (e.g. isopropyl; isobutyl; etc.), the substitute groups being, for instance, similar to those observed in the article by Ellen Hildebrandt et al. as cited above that were shown to inhibit bacterial endo-exonuclease activity when added to amidines that were described in the article, yet different to the amidines described herein, led to the discovery that these compounds not only exhibited human endo-exonuclease inhibitory activity, but showed comparable if not improved inhibition over pentamidine. As a result, amidine compounds containing several different substitute groups were synthesized, as described herein (e.g. methyl, isopropyl, isopropyl; isobutyl; etc.), and each exhibited significant human endo-exonuclease inhibition.

Overview

Therefore, the methods and compounds of the present disclosure can be useful in treating cancer (e.g. cancers characterized by exhibiting an increased level of endo-exonuclease activity). By treatment, it is meant that the compounds of the present disclosure inhibit the onset, growth, and/or spread of the cancer, cause regression of the cancer, cure the cancer and/or improve the condition of the patient afflicted with the cancer.

The compounds and methods disclosed herein are primarily directed to human patients. However, a skilled person in the art will readily understand that the compounds and methods disclosed herein may be directed to another subject, such as an animal, without departing from the present teachings.

As discussed above, the present application is directed to compounds of formula (I), pharmaceutically acceptable salts thereof, compounds of formula (II), and/or pharmaceutically acceptable salts thereof. These compounds may be provided in one or more pharmaceutically acceptable carriers for intravenous, aerosol, parenteral administration, etc.

Moreover, the dosage (therapeutically effective amount) to be administered will depend upon the weight of the patient, the severity of the disease, and the compound(s) to be administered. For instance, administering pentamidine, which has some structural similarities to the presently described amidine compounds, at amounts between 4 mg/kg to 7 mg/kg for two days every two weeks has been shown to be safe for patients.

It has been shown that administering 100 mg of pafuramidine orally twice daily for fourteen days to treat pneumocystis pneumonia led to concerns of kidney toxicity (Alison H. Harrill et al., "A Mouse Diversity Panel Approach Reveals the Potential for Clinical Kidney Injury Due to DB289 Not Predicated by Classical Rodent Models", *Toxicological Sciences* 130(2), 416-426 (2012)). It may be appreciated that, due to certain structural similarities between pafuramidine and the present amidine compounds, the present amidine compounds may show similar toxicity to pafuramidine. However, a level of toxicity, which might be problematic for treating a bacterial infection, would in fact be acceptable in the treatment of cancer. This would in fact be indicative that the present amidine compounds are within the tolerable toxicity range to treat cancer. The acceptable level of toxicity of the present amidine compounds is also further supported by the reduced frequency and reduced amount of compound administered to treat cancer versus administering a compound to treat a bacterial infection (where, in the study documented in the article by Harrill et al., the compound was administered daily for fourteen days—such long and frequent dosage regimens are not necessary to treat cancer as cancer treatment usually involves short cycles of chemotherapy).

Therefore, due to certain similarities in the molecular structure of pentamidine and pafuramidine to the present amidine compounds, a skilled person will readily recognize that the present amidine compounds may have similar levels of toxicity, or absence thereof, to pentamidine and pafuramidine. This level of toxicity may be acceptable to treat cancer. Moreover, due to their structural similarity with pentamidine, the present amidine compounds may also be administered at a similar dosage (or at a lesser dosage due to, in some cases, their observed increased activity when compared to pentamidine) to that set to treat cancer with pentamidine.

The present disclosure relates to the unexpected result that amidine compounds disclosed herein show inhibitory activity of endo-exonuclease.

Therefore, the above-described compounds of formula (I), pharmaceutically acceptable salts thereof, compounds of formula (II), and/or pharmaceutically acceptable salts thereof, or a combination thereof, may be administered to treat a subject with cancer, such as cancers having increased endo-exonuclease activity.

As a result, the present disclosure is also directed to a method of treating cancer, e.g., in a patient where the cancer cells have an increased level of endo-exonuclease activity in comparison to the endo-exonuclease activity of normal cells. The method involves administrating a therapeutically effective amount, to treat the cancer, of at least one of:
a compound of formula (I);
a pharmaceutically acceptable salt thereof;
a compound of formula (II), and
a pharmaceutically acceptable salt thereof.

In some examples, measuring the level of endo-nuclease activity and/or the presence thereof may be provided in the method using such techniques as immunoblotting, immunohistochemistry, immunoassay (e.g. ELISA), etc.

The following is a description of the study that led to the discovery of the presently-disclosed amidine compounds, and to the discovery that the above-described compounds of formula (I), pharmaceutically acceptable salts thereof, the above-described compounds of formula (II), and/or pharmaceutically acceptable salts thereof, or a combination thereof, inhibit endo-exonuclease activity. It will be understood that other techniques and/or protocols than those described herein may be used by a person of ordinary skill in the art to, for instance, measure endo-exonuclease activity or inhibition thereof by administering a given compound.

Exemplary Synthesis

The following describes an exemplary synthesis of a compound of formula (I):

Scheme 1: exemplary synthesis of a compound of formula (I)

An appropriate p-cyano-phenolic ether such as compound 1 is treated with hydrochloric acid in ethanol (anhydrous), and is stirred until no more product 2 formation is observed. Compound 2 is separated from the reaction mixture, and characterized for the formation of the imine.

Compound 2 is treated with an appropriate amine in anhydrous EtOH at room temperature, and the reaction is continued until completed. The solvent is removed and the crude compound 3 is washed with water, and dried into an anhydrous product. Compound 3 can further be converted into a hydrochloric acid salt by treating the product with HCl gas in anhydrous EtOH in an ice bath, and separating the resulting solid by first concentrating and precipitating with dry diethyl ether.

The following describes an exemplary synthesis of a compound of formula (II):

Scheme 2: exemplary synthesis of a compound of formula (II), where R2 is a hydrogen.

II

The synthetic strategy for the preparation of a compound of formula (II) consists of using p-bromophenol, and a nitrile moiety at the para position can be substituted to yield compound 5. The dinitrile 6 can be obtained by treatment of at least two equivalents of compound 5 with an appropriate alkyl dibromide or an alkyl dihalide or an alkyl reagent with two leaving groups, in the presence of a base to yield compound 6. Further reaction of 6 to convert the dinitrile into Species II can be accomplished by treatment with ethanol in the presence of HCl, followed by treatment with one equivalent of an appropriate amine (R2NH2), and then with ammonia in ethanol.

Scheme 3: exemplary synthesis of a compound of a formula (II).

III

Compound III can be obtained from compound 6, where compound 6 can be prepared using steps from Scheme 2. Reaction of compound 6 to convert the dinitrile into compound III can be accomplished by treatment with ethanol in the presence of HCl, followed by treatment with one equivalent of a first appropriate amine (R1NH2) and one equivalent of second appropriate amine (R2NH2). It will be understood that when R1 is equivalent to R2, at least two equivalents of an appropriate amine (R2NH2) may be used instead.

Compounds II and III can further be converted into the corresponding hydrochloric acid salts by treating the products with HCl gas in anhydrous EtOH in an ice bath, and separating the resulting solid by first concentrating and precipitating with dry diethyl ether. The resulting products will be the chloride salts of the respective compounds II and III, respectively. Similar salt forms, such as sulfate salt of compound II or compound III can be prepared by subjecting compound II or III to the appropriate inorganic or organic acid, or known procedures for the preparation of inorganic or organic salts of amidines and diamidines.

EXAMPLES

Cell lines from human colon adenocarcinoma (HT29), human breast adenocarcinoma (MCF7) and human cervical epithelioid carcinoma (HeLa) were obtained from the American Type Culture Collection (ATCC) and have ATCC accession numbers HTB-38, HTB-22, and CCL-2 respectively. The normal primary cell, NHDF, was obtained from Dr. Shirley Lehnert. These cells are normal human skin fibroblasts. The cells were grown in RPMI media supplemented with 10% FCS at 37° C. in a humidified incubator with 5% $CO_2$.

Example 1

Determination of Endo-Exonuclease Levels in Cells

Figure 1:
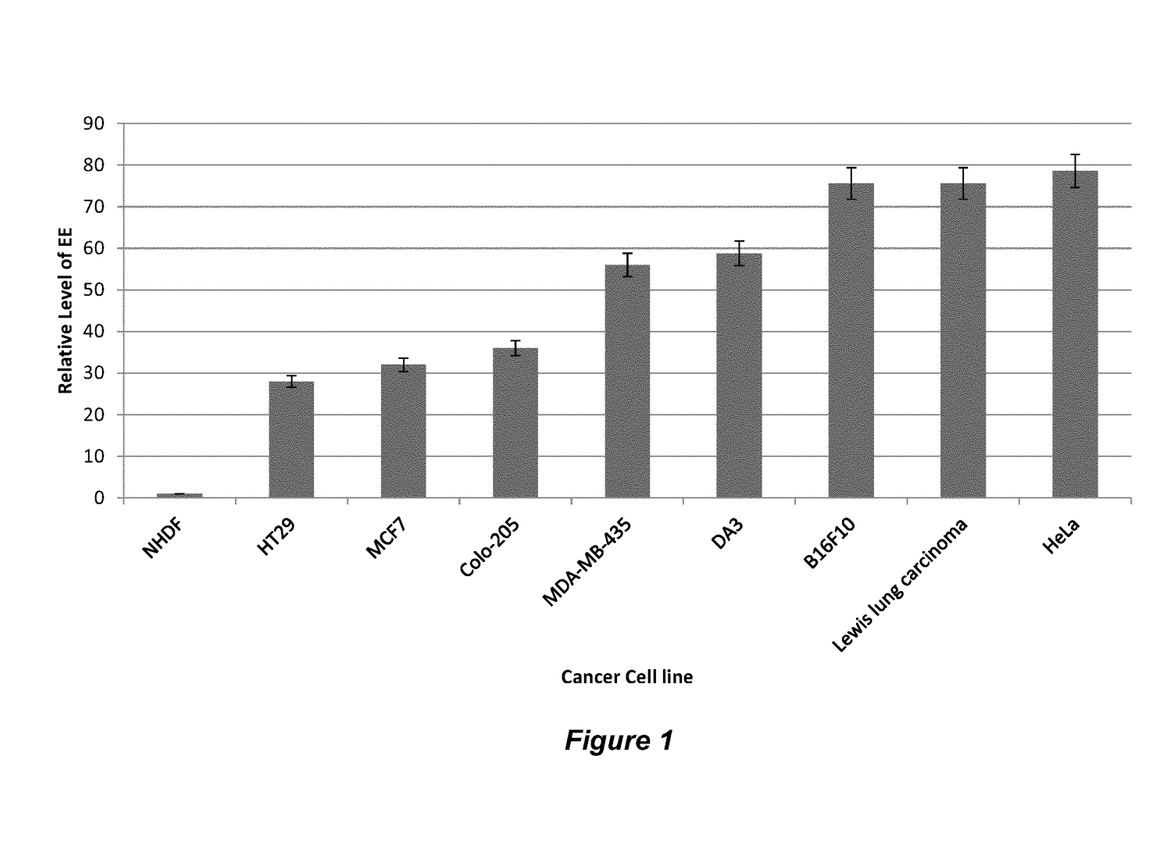
FIG. 1 is a graph showing the relative expression levels of endo-exonuclease activity in different cancer cell lines when compared to a normal, non-cancerous cell.

The human endo-exonuclease level in the cell lines was determined according to the Immuno-blot method as described by Chow and Resnick (1987) (full citation below). Exponentially growing cells were boiled in lysis buffer (0.125 M Tris-HCl pH 7.0, 20% glycerol, 4% SDS, 0.5 mM EDTA). The lysed cells were then centrifuged at 10,000 g for 10 min and 25 µl of the supernatant were electrophoresed on a 10% SDS-polyacrylamide gel (SDS-PAGE) according to the method described in Laemmli U. K., "Cleavage of structural proteins during the assembly of the head of bacteriophage T4", (1970) Nature 227(5259): 680-685. Proteins that had been separated on the SDS-PAGE gel were transferred electrophoretically to a nitrocellulose membrane. The nitrocellulose membrane was then reacted with rabbit antiserum raised against the monkey CV-1 endo-exonuclease in buffer B (10 mM Tris-HCl, pH 8.0, 1 mM EDTA, 150 mM NaCl) containing 0.5% skim-milk powder according to the method previously described by Chow and Resnick (1988). After the membrane had been washed three times in buffer B for 15 min., protein A (a polypeptide isolated from *Staphylococcus Aureus* that binds to the Fc region of the immunoglobulin molecules without interacting at the antigen binding site) conjugated with horseradish peroxidase in buffer B containing 0.5% skim-milk powder was added to the membrane and incubated for 3 h at room temperature. The membrane was subsequently washed with buffer B for 15 min. Positive signals were indicated by colour development of the substrate 4-chloro-1-naphthol at the corresponding protein position in the horseradish peroxidase enzymatic reaction. Relative amounts of positive signals were detected using a HP4c scanner and its corresponding scanner program. Based on this method, the endo-exonuclease levels in normal cells and the HT29, MCF-7 and HeLa cell lines were calculated. The results presented in the sole Figure show that the level of the endo-exonuclease is much higher in these cancer cells than in normal cells. These results suggest that inhibition of the endo-exonuclease enzyme should provide a means of preferentially attacking cancer cells. In addition, the results suggest that measurement of enzyme concentrations in body fluids or tissues provides a means of detecting cancer and of monitoring its progress.

Example 2

Determination of Cell Survival

Cell survival was determined according to the following methods:

Cell Survival—MTT assay: The MTT (3-[4,5-Dimethyl-thiazol-2-yl]-2,5 diphenyl tertrazolim bromide) method of determining cell growth/cytotoxicity is used to determine cell survival. MIT is a tetrazolium salt cleaved by mitochondrial dehydrogenases of living cells. Cleavage converts yellow, water soluble MTT to an insoluble, purple formazan crystal. The crystals can be solubilized with a 50% N,N-dimethylformamide (vol/vol), 20% SDS (wt/vol) solution (pH 4.7), and absorbance determined at a wavelength of 570 nm. Dead cells will not cleave MTT and uncleaved MTT is not detectable at this wavelength. The amount of MTT that is cleaved increases with increasing cell numbers, and decreases as a result of cell cytotoxicity (Niks and Otto 1990, Hussain et al. 1993). Cells were harvested from cell cultures using a standard protocol (i.e. Trypsin/EDTA). The cells (1000 to 5000 cells depending on cell type in 50 µl) were then plated and incubated overnight at 37° C. The compound (e.g. the compound of formula (I); compound of formula (II); pentamidine; or the vehicle) was introduced. After 2 days of incubation at 37° C., 10 µl of a 5 mg/ml solution of MTT was then added to all the experimental wells as well as the media control well. The plates were further incubated for 4 hours. MTT solubilization buffer (100 µl) was then added and the plates were incubated overnight at 37° C. The plates were then read on an ELISA plate reader with absorbance at 570 nm and a reference at 630 nm.

Example 3

Endo-Exonuclease Isolation and Assay

The human endo-exonuclease was isolated according to the method described by Liu and Chow et al (1995). The cultured cells were detached with trypsin-EDTA and the cell suspensions were centrifuged at 4° C. with a force of 700 g for 10 minutes. The cell pellets were washed twice with cold phosphate buffered saline (PBS). The cells were then resuspended and sonicated in 20 mM Tris-HCl, pH 7.5, containing 5 mM EDTA and 1 mM PMSF (buffer A). The resulting cell lysis suspensions were centrifuged at 4° C. at 10,000 g for 15 min. The supernatants were then loaded onto an antibody-protein A-Sepharose affinity column, as previously described by Chow and Resnick (1987). After washing extensively with buffer A (i.e. until the $A_{280}$ of the eluates were zero), the column was then eluted with buffer A containing 3.5 M $MgCl_2$ to elute the endo-exonuclease. The eluted endo-exonuclease was dialyzed extensively against buffer A with at least two changes of buffer and one change of distilled water. The endo-exonuclease was then concentrated by lyophilization.

The endo-exonuclease activities were determined by measuring the digestion of circular plasmid DNA following the exemplary set of steps. Superhelical pBR322 DNA (or YEp DNA) was treated with endo-exonuclease at 37° C. Reactions were stopped by the addition of a solution containing 5 mM EDTA, 1% SDS, 30% glycerol, and bromophenol blue. The resulting mixtures were then loaded onto a 0.7% agarose gel and electrophoresed for 3 hours at 70 V. The gels were stained with 100 ml of 0.5 µg/ml ethidium bromide solution. Endo-exonuclease activities were measured as the rate of conversion from RFI to RFII to RFIII and subsequent fragments.

For the inhibition assay, pentamidine, mono-amidine compounds according to the present teachings and di-amidine compounds according to the present teachings were added to the endo-exonuclease prior to the start of the nuclease reaction. In order to arrive at the measurements related to the % of cell growth of H661, the MTT assay as described above was performed. The resulting endo-exonuclease inhibition is shown in the Table 1 and Table 2 that follow:

TABLE 1 effect of inhibitor compounds (amidine compounds) on endo-exonuclease activity and cell growth of the lung cancer cell H661. The inhibitor compounds used herein were pentamidine, and "mono-amidine A", which corresponds to a compound of formula (I) where R3 is —$CH_3$ (a methyl group), R4 is "H" and "n" equals "1".

| Compound | Endo-exonuclease Inhibition at 50 µM (%) | H661 (Lung Cancer Cell) (% of Cell Growth at 2.5 µM) |
|---|---|---|
| Vehicle | 0 | 100 |
| Pentamidine | 50 | 20 ± 2 |
| Mono-amidine A | 60 | −30 ± 5* |

*The negative value observed for the mono-amidine A is due to cell killing (death) in addition to growth inhibition, as measured by the MTT assay. In one example, the vehicle may be water.

As shown in Table 1, mono-amidine A showed increased inhibition of endo-exonuclease activity when compared to pentamidine. In fact, the uptake of mono-amidine A into the lung cancer cells not only slowed the cell growth of the cancer cells, but also led to the apoptosis of the cancer cells, as shown by the negative value in Table 1, indicative of a reduction of cancer cells in the sample. Death of the cancer cells was not observed when pentamidine, another endo-exonuclease inhibitor, was administered.

The number of lung cysts remaining in the samples provided with endo-exonuclease inhibitors was obtained according to the following protocol.

Example 4

Lewis Lung cancer cells are injected subcutaneously into standard laboratory mice (i.e. nude mice). Thereafter, they rapidly formed solid tumours. The sizes of the tumours can be measured. Although the injected cells are derived from lung cancers, the tumours actually grow in the back of the mice. All animals were inoculated at the same site.

Primary tumours were allowed to grow until they were 0.5-1.0 $cm^3$ in size. At this point, cells from the tumours start circulating in the blood streams of the mice. These circulating cells have the capacity to form secondary tumours in the lung.

The primary tumours are removed surgically from the mice. The mice are then treated with the amidine compounds so as to try and control the growth of secondary tumours. The extent to which control has been achieved is measured by sacrificing the mice and by physically counting the new tumours that can be seen growing on the surfaces of the lungs. The results are presented in Table 2 found below.

TABLE 2 effect of inhibitor compounds (amidine compounds) on endo-exonuclease activity and on the inhibition and disappearance of lung cysts. The inhibitor compounds used herein were pentamidine, "di-amidine A", which corresponds to a compound of formula (II) and "di-amidine B", which also corresponds to a compound of formula (II). In di-amidine A, both R1 and R2 of formula (II) are phenyl, and "n" equals 5. In di-amidine B, both R1 and R2 are isopropyl, and "n" equals 5.

| Compound | Endo-exonuclease Inhibition (IC50, µM) | Lung Cysts remaining (% of Control) |
|---|---|---|
| Pentamidine | 50 | 4.5 |
| Di-Amidine A | 58 | 1.7 |
| Di-Amidine B | 14 | 0.22 |

In the experiment leading to the results presented in Table 2, pentamidine, di-amidine A and di-amidine B were each respectively introduced into cancer cells. Di-amidine A required 58 µM in order to reach 50% inhibition of endo-exonuclease activity. This is comparable to pentamidine, where 50 µM was needed in order to reach 50% inhibition of endo-exonuclease activity. However, di-amidine A was more effective in reducing the number of lung cysts than pentamidine (1.7% for di-amidine A vs. 4.5% for pentamidine). In contrast, a lesser concentration of di-amidine B (14 µM) was required to inhibit endo-exonuclease activity by 50% more than pentamidine. Moreover, after di-amidine B was administered, most of the lung cysts were no longer apparent, with only 0.22% remaining.

Example 5

Cell Survival in the Presence of Mono- and Di-Amidines

The rates of survival of H661 lung cancer cells in the presence of pentamidine and mono-amidine A, which were obtained by performing the MTT assay as described above, are shown in the above Table 1. The mono-amidine A preferentially attacks cancer cells in a dose dependent manner as further shown in Example 6 described below.

Example 6

Anti-Cancer Activity

The anticancer activities of the mono-amidine A are shown in the above Table 1.

In Table 1, the cancer cell type H661 is more sensitive to the mono-amidine than the pentamidine control and is dose dependent.

The clinical use of these agents depends upon a balance between anticancer activity and harmful side effects. Thus, a relatively non-toxic agent, which can be given in high concentration may be more effective than a more aggressive but toxic agent which can only be tolerated in very small doses. Based on known clinical data, pentamidine has low toxicity. Similarly, the mono-amidines and di-amidines described herein also likely similarly show low toxicity as a function of concentration due, for instance, to their molecular similarity to pentamidine and certain furan-based antibiotics used to inhibit bacterial endo-exonuclease activity. Furthermore, as these mono-amidines and di-amidines have been shown to be more potent than pentamidine; in some examples, administering lesser amounts of the compound is necessary to inhibit the spread of cancer cells or tumor growth. Moreover, even though certain compounds are considered to have a toxicity level that is too elevated to treat certain bacterial infections, these compounds may still have tolerable toxicity levels to treat cancer as a result of the severity and risks tied to the disease, as well as the longer intervals between administrations.

The results presented in the above Tables 1 and 2 show that mono- and di-amidine inhibitors of the present disclosure inhibit endo-exonuclease and have anti-cancer activity.

Tables 3, 4 and 5 show that mono- and di-amidine inhibitors of endo-exonuclease are anti-cancer agents and exhibit synergistic anti-cancer activity when used in combination with standard chemotherapeutic agents. The MTT assay as described above was performed on the H460 Lung Carcinoma Cell Line, the HT29 Colon Cancer Cell Line and the MCF7 Breast Cancer Cell Line with various amounts of the above-described di-amidine A, either alone or together with a chemotherapeutic agent selected from Iniparib, Veliparib and Olaparib, to achieve the results presented in Table 3, Table 4 and Table 5, respectively. Iniparib, Veliparib and Olaparib were also subjected to the MTT assay without an endo-exonuclease compound as controls.

TABLE 3

MTDX101 and PARP Inhibitors on H460 Lung Carcinoma Cell Line. MTDX101 is the di-amidine A described above with regard to Table 2.

| | % Inhibition | ±Average deviation |
|---|---|---|
| MTDX101 (33 µM) | 25 | ±16 |
| MTDX101 (336 µM) | 85 | |
| Iniparib (42 µM) | 0.8 | ±1 |
| Veliparib (50 µM) | 19 | ±11 |
| Olaparib (73 µM) | 11 | ±7 |
| Iniparib (42 µM) + MTDX101 (33 µM) | 79 | |
| Veliparib (50 µM) + MTDX101 (33 µM) | 80 | ±20 |
| Olaparib (73 uM) + MTDX101 (33 µM) | 97 | ±3 |
| Iniparib (42 uM) + MTDX101 (336 µM) | 99.8 | ±0.4 |
| Veliparib (50 uM) + MTDX101 (336 µM) | 99 | ±1 |
| Olaparib (73 µM) + MTDX101 (336 µM) | 100 | ±0 |

TABLE 4

MTDX101 and PARP Inhibitors on HT29 Colon Cancer Cell Line. MTDX101 is the di-amidine A described above with regard to Table 2.

| | % Inhibition | ±Average deviation |
|---|---|---|
| MTDX101 (33 µM) | 15 | |
| MTDX101 (336 µM) | 64 | |
| Iniparib (42 µM) | 4.8 | ±2.8 |
| Veliparib (50 µM) | 6 | ±4 |
| Olaparib (73 µM) | 14 | ±19 |
| Iniparib (42 µM) + MTDX101 (33 µM) | 29.8 | ±15 |
| Veliparib (50 µM) + MTDX101 (33 µM) | 31.3 | ±14 |
| Olaparib (73 uM) + MTDX101 (33 µM) | 67 | ±8.7 |
| Iniparib (42 uM) + MTDX101 (336 µM) | 99 | ±1 |
| Veliparib (50 uM) + MTDX101 (336 µM) | 98 | ±0.5 |
| Olaparib (73 µM) + MTDX101 (336 µM) | 99 | ±1.3 |

TABLE 5

MTDX101 and PARP Inhibitors on MCF7 Breast Cancer Cell Line. MTDX101 is the di-amidine A described above with regard to Table 2.

| | % Inhibition | ±Average deviation |
|---|---|---|
| MTDX101 (33 µM) | 20 | |
| MTDX101 (336 µM) | 80 | |
| Iniparib (42 µM) | 5 | ±5.3 |
| Veliparib (50 µM) | 13 | ±9.8 |
| Olaparib (73 µM) | 17 | ±12 |
| Iniparib (42 µM) + MTDX101 (33 µM) | 56 | ±20 |
| Veliparib (50 uM) + MTDX101 (33 µM) | 64 | ±12 |
| Olaparib (73 uM) + MTDX101 (33 µM) | 54 | ±8.4 |
| Iniparib (42 uM) + MTDX101 (336 µM) | 99.8 | ±0.4 |
| Veliparib (50 uM) + MTDX101 (336 µM) | 99.5 | ±0.5 |
| Olaparib (73 µM) + MTDX101 (336 µM) | 99.7 | ±0.4 |

Statistical Analysis

The two-tailed Student T-test was used to compare statistical significance amongst various groups.

Results

Effect of Mono- and Di-Amidine on the Growth of Cancer Cells

As was explained above, several experiments were performed to examine the anti-tumour properties of mono- and di-amidines according to the present teachings i.e. on the growth of cancer cells, when compared to pentamidine, a known anti-cancer agent. These experiments indicate that the mono- and di-amidines of the present teachings are better endo-exonuclease inhibitors and more potent anti-cancer agents than pentamidine. At the same concentration of 50 μM, the mono- and di-amidines of the present teachings are more effective at inhibiting cancer cell growth and resulting in cancer cell death (Tables 1 and 2).

Example 7

YEp DNA was used as a substrate for measuring the inhibition of endo-exonuclease activity. The assay was conducted in accordance with the procedure described in Example 3 relating to endo-exonuclease isolation and assay. Results are presented in FIG. 2.

Figure 2:
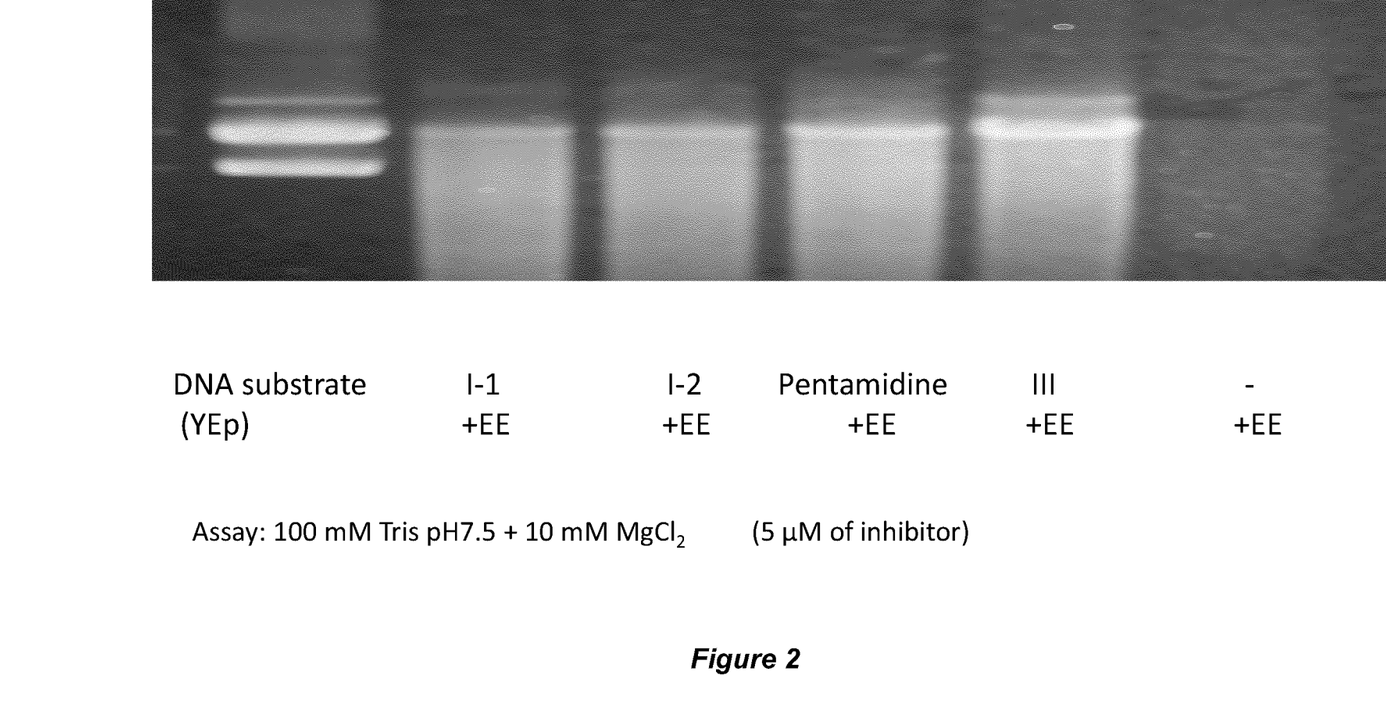
FIG. 2 is a picture of agarose gel results illustrating endo-exonuclease-inhibition activity by mono-amidine and di-amidine compounds comparing to pentamidine.

As shown in FIG. 2, without the presence of the inhibition compound, endo-exonuclease degrades the YEp DNA. Adding the inhibition compound results in preserving some of the DNA, where a thicker, denser band is an indication that less DNA has broken down, indicating an increased inhibition of endo-exonuclease activity.

The inhibition of endo-exonuclease by compounds I, II and III was measured and compared to the inhibition of pentamidine. The molecular structures of compounds I, II and III are as follows:

For monoamidine compounds (I-1) and (I-2), R3 is respectively isopropyl and isobutyl. For the diamidine compound (III), R1 and R2 are both isopropyl. However, it will be understood that R1 and R2 of the diamidine compound could equally be isobutyl (as substituting the sp3 nitrogen of the monoamidine compound with isobutyl appears to result in similar inhibition to when the same nitrogen is substituted with isopropyl—and as such, inhibition observed between a diamidine compound with isobutyl as R1 and R2 and a diamidine compound with isopropyl as R1 and R2 should also be similar).

As shown in FIG. 2, the presence of monoamidine compound I-1 or monoamidine compound I-2 resulted in similar endo-exonuclease inhibition to pentamidine. The presence of the diamidine compound III resulted in a greater inhibition of endo-exonuclease activity than pentamidine, as indicated by the thicker band when diamidine compound III was introduced.

As such, based on the results presented in FIG. 2, it is noted that the mono-amidine and di-amidine compounds are as good as and/or better than pentamidine in inhibiting endo-exonuclease activity.

It will be appreciated that even though the present study presented, as examples, the effects of the mono-amidines and di-amidines on certain types of cancer cells, the mono- and di-amidines of the present teachings may be used to inhibit proliferation of, growth of, and/or treat cancer corresponding to different cancer cell lines, such as those, e.g., presented in FIG. 1, having increased human endo-exonuclease activity, by targeting the human endo-exonuclease.

Discussion

An abnormal (elevated) level of endo-exonuclease was detected in almost all the patient samples whereas the standard cancer diagnostic marker, CEA, gave positive results in only approximately 25% of the same patient samples.

This study indicates that mono- and di-amidines of the present teachings inhibit cancer cell growth.

This study indicates that mono- and di-amidines of the present teachings inhibit human endo-exonuclease activity.

Moreover, the combination of mono- and di-amidines of the present teachings with known chemotherapy drugs clearly improves the therapeutic response in light of the data described above.

The study shows that mono- and di-amidines of the present teachings, where the group (R3) substituting the hydrogen that was attached to the sp3 nitrogen of the amidine group of mono-amidine, or where the group substituting the hydrogen that was attached to the sp3 nitrogen of respectively one or both of the amidine groups of diamidine (R1 and/or R2) lead to mono-amidine and di-amidine compounds having endo-exonuclease inhibition (e.g. human endo-exonuclease activity). The present study focused on certain substitute groups attached to the sp3 nitrogen of the amidine group of mono-amidine and di-amidine, as illustrated in Tables 1 and 2. The substitute groups varied in terms of their molecular structure (i.e. a methyl group, a phenyl group, an isopropyl group, an isobutyl group). This study therefore shows that replacing the H attached to the sp3 nitrogen of the amidine group leads to mono-amidine and di-amidine compounds with increased human endo-exonuclease inhibition. Therefore, it will be understood, shown by the data herein, that other substitute groups at the position of the H attached to sp3 nitrogen of the amidine group may be used, without departing from the present teachings. Additionally, it will also be appreciated, that the substitute groups of R1, R2 and R3 may be selected from a loweralkyl without departing from the present teachings. Moreover, it will be appreciated that other substitute groups at the position of the H attached to sp3 nitrogen of the amidine group may be used while still conferring human endo-exonuclease activity as it is shown herein that the size and/or nature of the substitute group may vary significantly while still showing endo-exonuclease activity (e.g. the size of a methyl group versus the size of the phenyl group, where, for instance, a phenyl group leads to more steric hindrance than the methyl group). Finally, it will be further understood that although the examples of Table 2 show di-amidine compounds where both R1 and R2 are substituted, in some examples, only R1 or R2 may be substituted as described herein while still demonstrating increased endo-exonuclease inhibition. As shown with the endo-exonuclease inhibition observed with the mono-amidine compound, only one end of the di-amidine compound is needed to play a role in inhibiting endo-exonuclease activity, as it appears that the amidine moiety interacts with the endo-exonuclease active site. Therefore, a substitute group may be present at either R1 or R2, or, at both R1 and R2.

R5 of the compound of formula II may be a carbon chain. In some embodiments, the carbon chain consists of five carbons. However, it will be understood that the length of the carbon chain may have more or less than five carbons without departing from the present teachings, as it is R1 and/or R2 that appear to significantly contribute to the endo-exonuclease inhibitory activity of the compound of formula II. The carbon chain may be saturated or unsaturated (there may be one or more double or triple bonds). R5 may be unsubstituted or substituted.

Pharmaceutical Compositions

Pharmaceutical compositions of the above compounds are used to treat patients having cancer. Vehicles for delivering the compounds of the present application to target tissues throughout the human body include saline and D5W (5% dextrose and water). Excipients used for the preparation of oral dosage forms of the compounds of the present application include additives such as a buffer, solubilizer, suspending agent, emulsifying agent, viscosity controlling agent, flavor, lactose filler, antioxidant, preservative or dye. There are preferred excipients for parenteral and other administration. These excipients include serum albumin, glutamic or aspartic acid, phospholipids and fatty acids.

In some embodiments, the preferred storage state is freeze-dried, yielding a powdered form. The preferred administration formulation is in liquid form stored in a vial or an intravenous bag. The compounds of the present disclosure may also be formulated in solid or semisolid form, for example pills, tablets, creams, ointments, powders, emulsions, gelatin capsules, capsules, suppositories, gets or membranes. The preferred route of administration is intravenous. Other acceptable routes of administration include oral, topical, rectal, parenteral (injectable), local, inhalant and epidural administration. The pharmaceutical compositions may also be conjugated to transport molecules or included in transport modalities such as vesicles and micelles to facilitate transport of the molecules. Methods for the preparation of pharmaceutically acceptable compositions that can be administered to patients are known in the art.

The pharmaceutical compositions may also be conjugated to transport molecules, monoclonal antibodies or transport modalities such as vesicles and micelles that preferentially target cancer cells or that potentiate cancer cells to receive drugs.

Pharmaceutical compositions including the compounds of the present disclosure can be administered to humans or animals. Dosages to be administered depend on the individual patient condition, indication of the drug, physical and chemical stability of the drug, toxicity, the desired effect and on the chosen route of administration (Robert Rakel, ed., Conn's Current Therapy (1995, W.B. Saunders Company, USA)). These pharmaceutical compositions are used to treat cancer.

Conclusions

It was previously known that amidines have anti-fungal and anti-microbial activity. It has been found that mono- and di-amidines of the present teachings inhibit the activity of endo-exonuclease sufficiently to stop the growth of cancer cell lines in vitro. Mono- and di-amidines of the present teachings are also expected to slow tumour growth in animals with very aggressive cancers, certainly based on the potency of the compounds examined herein when compared to pentamidine, which has already been shown to slow tumour growth in animals with very aggressive cancers.

Although the invention has been described with reference to preferred embodiments, it is to be understood that modifications may be resorted to as will be apparent to those skilled in the art. Such modifications and variations are to be considered within the purview and scope of the present invention.

Representative, non-limiting examples of the present invention were described above in detail with reference to the attached drawing. This detailed description is merely intended to teach a person of skill in the art further details for practicing preferred aspects of the present teachings and is not intended to limit the scope of the invention. Furthermore, each of the additional features and teachings disclosed above and below may be utilized separately or in conjunction with other features and teachings to provide useful amidine and diamidine compounds and methods of treating cancer using the same.

Moreover, combinations of features and steps disclosed in the above detailed description, as well as in the experimental examples, may not be necessary to practice the invention in the broadest sense, and are instead taught merely to particularly describe representative examples of the invention. Furthermore, various features of the above-described representative examples, as well as the various independent and dependent claims below, may be combined in ways that are not specifically and explicitly enumerated in order to provide additional useful embodiments of the present teachings.

All features disclosed in the description and/or the claims are intended to be disclosed separately and independently from each other for the purpose of original written disclosure, as well as for the purpose of restricting the claimed subject matter, independent of the compositions of the features in the embodiments and/or the claims. In addition, all value ranges or indications of groups of entities are intended to disclose every possible intermediate value or intermediate entity for the purpose of original written disclosure, as well as for the purpose of restricting the claimed subject matter.

REFERENCES

Chow, T. Y.-K., and Resnick, M. A. (1983) The identification of a deoxyribonuclease controlled by the RAD52 gene of

What is claimed is:

1. A method of treating one or more of colon cancer, breast cancer, cervical cancer and lung carcinoma through endo-exonuclease inhibition by administering a compound having the formula:

wherein:
R1 is isopropyl;
R2 is isopropyl; and
R5 is a loweralkyl comprising a linear carbon chain of at least two carbons.

2. The method as defined in claim 1, wherein R5 is $(CH_2)_n$, and wherein n is equal to an integer from 2 to 7 inclusively.

3. The method as defined in claim 2, wherein n equals 5.